US012734296B2

(12) United States Patent
Myrman

(10) Patent No.: US 12,734,296 B2
(45) Date of Patent: Sep. 15, 2026

(54) DELIVERY DEVICE FOR A FLEXIBLE LIQUID CONTAINER

(71) Applicant: SHL MEDICAL AG, Zug (CH)

(72) Inventor: Mattias Myrman, Tyreso (SE)

(73) Assignee: SHL Medical AG, Zug (CH)

( * ) Notice: Subject to any disclaimer, the term of this patent is extended or adjusted under 35 U.S.C. 154(b) by 537 days.

(21) Appl. No.: 18/267,220

(22) PCT Filed: Dec. 9, 2021

(86) PCT No.: PCT/EP2021/084900

§ 371 (c)(1),
(2) Date: Jun. 14, 2023

(87) PCT Pub. No.: WO2022/135945

PCT Pub. Date: Jun. 30, 2022

(65) Prior Publication Data

US 2024/0091451 A1 Mar. 21, 2024

(30) Foreign Application Priority Data

Dec. 21, 2020 (EP) .................................... 20216096

(51) Int. Cl.
*A61M 5/24* (2006.01)
*A61M 5/315* (2006.01)
*A61M 5/31* (2006.01)

(52) U.S. Cl.
CPC ........ *A61M 5/2425* (2013.01); *A61M 5/3158* (2013.01); *A61M 2005/314* (2013.01); *A61M 2005/3152* (2013.01)

(58) Field of Classification Search
CPC ................ A61M 5/2425; A61M 5/282; A61M 5/14586; A61M 5/148; A61M 5/31575; A61M 2005/3152
See application file for complete search history.

(56) References Cited

U.S. PATENT DOCUMENTS 401,950 A 4/1889 Haussmann
4,019,655 A 4/1977 Moeller
(Continued)

FOREIGN PATENT DOCUMENTS

CN 111225699 A 6/2020
EP 2796157 B1 9/2016
(Continued)

OTHER PUBLICATIONS

International Search Report and Written Opinion for Int. App. No. PCT/EP2021/084900, mailed Mar. 7, 2022.

*Primary Examiner* — Kami A Bosworth
*Assistant Examiner* — Mahmood Farooq
(74) *Attorney, Agent, or Firm* — McDonnell Boehnen Hulbert & Berghoff LLP

(57) ABSTRACT

A delivery device for delivering liquid from a flexible container is presented having a housing having a first wall provided with a housing first linear gear having housing first linear gear teeth, the housing being configured to receive the flexible container, a first roller having a first compound gear having a first gearwheel provided with first gearwheel teeth and a second gearwheel provided with second gearwheel teeth, and an actuator comprising an actuator first linear gear provided with actuator first linear gear teeth, wherein the first gearwheel teeth are configured to mesh with the housing first linear gear teeth and the second gearwheel teeth are configured to mesh with the actuator first linear gear teeth, wherein the actuator is configured to be moved linearly from a first position to a second position along a longitudinal axis defined by the longitudinal extension of the housing first linear gear.

17 Claims, 4 Drawing Sheets

(56) References Cited

U.S. PATENT DOCUMENTS

| | | | | |
|---|---|---|---|---|
| 6,547,099 | B1 | 4/2003 | Farris | |
| 6,669,668 | B1 * | 12/2003 | Kleeman | A61M 5/148 |
| 6,808,507 | B2 | 10/2004 | Roser | |
| 8,652,108 | B2 | 2/2014 | Basso et al. | |
| 8,672,879 | B2 | 3/2014 | Grant et al. | |
| 8,690,836 | B2 | 4/2014 | Mathews et al. | |
| 9,849,247 | B2 | 12/2017 | Taylor et al. | |
| 10,155,088 | B2 | 12/2018 | Basile | |
| 10,500,338 | B2 | 12/2019 | Berenshteyn | |
| 2011/0270220 | A1 | 11/2011 | Genosar | |
| 2014/0066846 | A1 | 3/2014 | Genosar | |
| 2018/0243505 | A1 | 8/2018 | Genosar | |
| 2019/0255254 | A1 | 8/2019 | Wilmot et al. | |
| 2020/0254182 | A1 | 8/2020 | Mathews et al. | |
| 2020/0297580 | A1 * | 9/2020 | Liscio | A61M 5/2425 |

FOREIGN PATENT DOCUMENTS

| | | | |
|---|---|---|---|
| EP | 2473218 | B1 | 10/2017 |
| JP | 2005-027831 | A | 2/2005 |
| JP | 2011-212184 | A | 10/2011 |
| WO | 2010/068415 | A1 | 6/2010 |
| WO | 2010/133673 | A1 | 11/2010 |
| WO | 2010/145786 | A1 | 12/2010 |
| WO | 2011/109840 | A2 | 9/2011 |
| WO | 2012/064761 | A2 | 5/2012 |

* cited by examiner

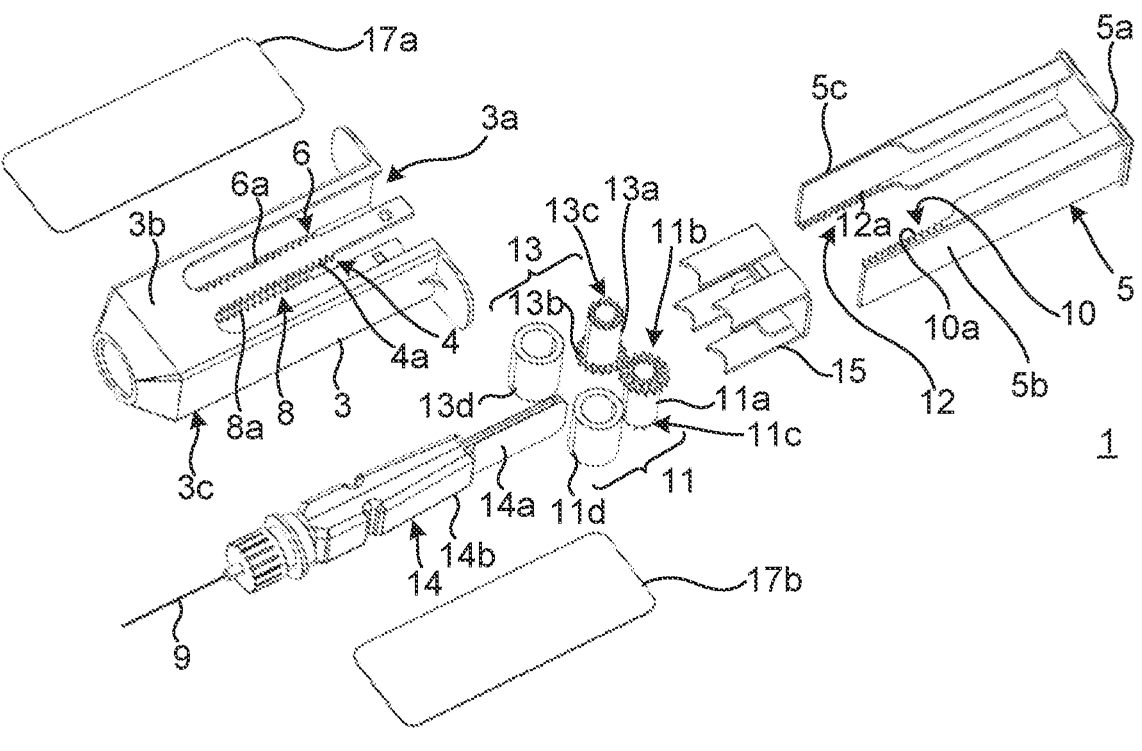
Fig. 2
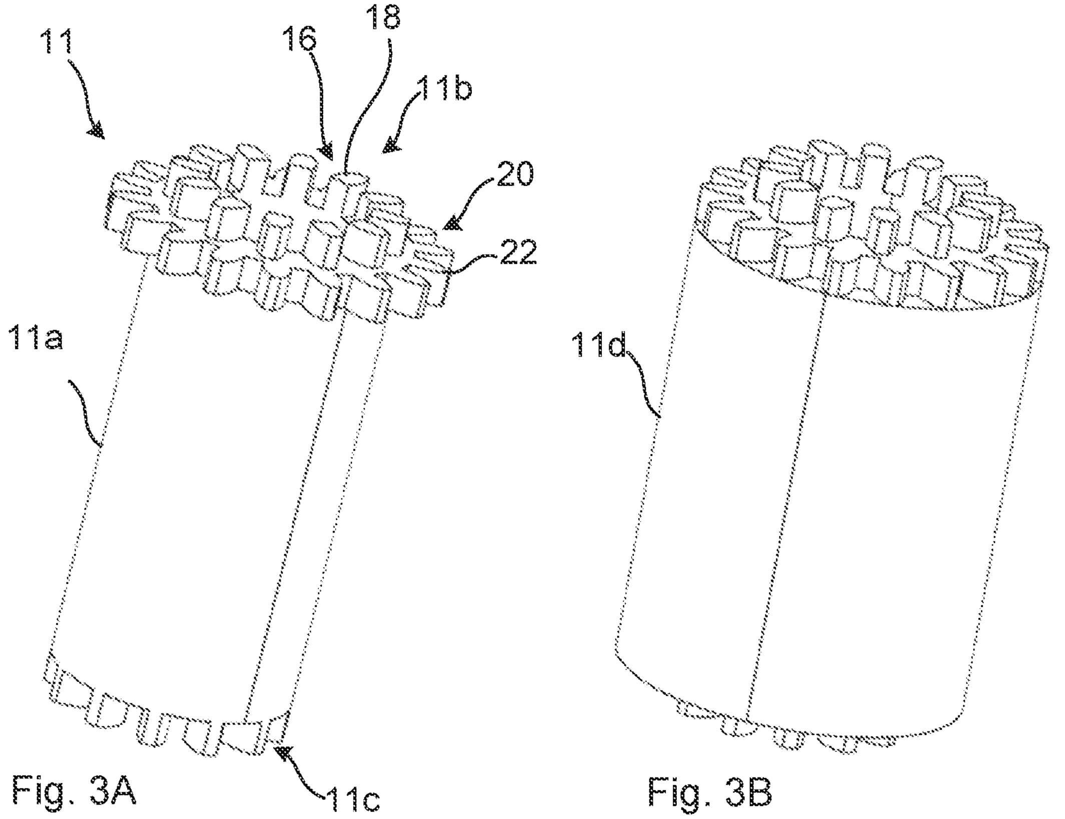
Fig. 3A
Fig. 3B

DELIVERY DEVICE FOR A FLEXIBLE LIQUID CONTAINER

CROSS REFERENCE TO RELATED APPLICATIONS

The present application is a U.S. National Phase Application pursuant to 35 U.S.C. § 371 of International Application No. PCT/EP2021/084900 filed Dec. 9, 2021, which claims priority to European Patent Application No. 20216096.6 filed Dec. 21, 2020. The entire disclosure contents of these applications are herewith incorporated by reference into the present application.

TECHNICAL FIELD

The present disclosure generally relates to delivery devices for dispensing liquid from a flexible container.

BACKGROUND

Some liquid containers may be mechanically flexible or soft. A blow-fill-seal container is an example of a common type of flexible container containing liquid.

Delivery devices may be used to facilitate delivery of the liquid content of a flexible container.

EP2796157 B1 discloses an auto-injector apparatus for delivering a liquid medicament from a flexible container. The apparatus comprises a container carriage supporting the flexible container. The carriage is provided with two slots that receive a respective axle of a roller. The entire carriage, including the flexible container with its needle, is initially moved forward by means of an assembly comprising drive racks and a drive gear to cause auto-penetration. As a result of the translation of the carriage, the roller is set free to move forward in the slot by means of a constant force spring. The roller thus moves over the flexible container and the medicament in the flexible container is dispensed.

The apparatus presented in EP2796157 is relatively complex. Moreover, it requires a large spring force for expelling high viscosity liquid medicaments.

SUMMARY

An object of the present disclosure is to provide a delivery device which solves, or at least mitigates problems of the prior art.

There is hence provided a delivery device for delivering liquid from a flexible container, the delivery device comprising: a housing having a first wall provided with a housing first linear gear having housing first linear gear teeth, the housing being configured to receive the flexible container, a first roller having a first compound gear comprising a first gearwheel provided with first gearwheel teeth and a second gearwheel provided with second gearwheel teeth, and an actuator comprising an actuator first linear gear provided with actuator first linear gear teeth, wherein the first gearwheel teeth are configured to mesh with the housing first linear gear teeth and the second gearwheel teeth are configured to mesh with the actuator first linear gear teeth, wherein the actuator is configured to be moved linearly from a first position to a second position along a longitudinal axis defined by the longitudinal extension of the housing first linear gear, causing the first roller to be translated along the housing first linear gear, to squeeze liquid from the flexible container, wherein the first gearwheel has a diameter which differs from that of the second gearwheel.

The design is simple and moreover provides a mechanical advantage due to the different amount of first gearwheel teeth and second gearwheel teeth.

With the term "compound gear" is meant two adjacently arranged gearwheels arranged coaxially, and fixed relative to each other. For example, the first gearwheel and the second gearwheel are arranged adjacently, coaxially, and fixed relative to each other.

The term "diameter" as used refers to the outer diameter of the gearwheels.

The first gearwheel may be arranged axially outside the second gearwheel at one axial end of the first roller.

According to one embodiment the diameter of the first gearwheel is smaller than that of the second gearwheel. The speed with which the first roller moves along the housing first linear gear will thereby be slower than that of the actuator. The torque provided by the first roller will however be amplified. The delivery device can thereby deliver liquids with high viscosity from the flexible container with less force required for operating the actuator.

According to one embodiment the housing has a second wall, opposite to the first wall, provided with a housing second linear gear having housing second linear gear teeth, and wherein the first roller has a third gearwheel provided with third gearwheel teeth configured to mesh with the housing second linear gear teeth.

According to one embodiment the first wall is provided with a housing third linear gear arranged parallel with the housing first linear gear, the housing third linear gear being provided with housing third linear gear teeth, wherein the delivery device comprises a second roller arranged parallel with the first roller and having a fourth gearwheel provided with fourth gearwheel teeth configured to mesh with the housing third linear gear teeth.

According to one embodiment the second wall is provided with a housing fourth linear gear arranged parallel with the housing second linear gear, the housing fourth linear gear being provided with housing fourth linear gear teeth, wherein the second roller has a second compound gearwheel comprising a fifth gearwheel provided with fifth gearwheel teeth and a sixth gearwheel provided with sixth gearwheel teeth, wherein the actuator has an actuator second linear gear provided with actuator second linear gear teeth, wherein the fifth gearwheel teeth are configured to mesh with the housing fourth linear gear teeth and the sixth gearwheel teeth are configured to mesh with the actuator second linear gear teeth, wherein movement of the actuator from the first position to the second position causes the second roller to be translated along the housing second linear gear to squeeze liquid from the flexible container from the opposite side relative to the first roller, and wherein the diameter of the fifth gearwheel differs from that of the sixth gearwheel.

The fifth gearwheel may be arranged axially outside the sixth gearwheel at one axial end of the second roller.

According to one embodiment the diameter of the fifth gearwheel is smaller than that of the sixth gearwheel.

According to one embodiment the actuator comprises an actuator third linear gear provided with actuator third linear gear teeth, and wherein the first roller has a seventh gearwheel provided with seventh gearwheel teeth configured to mesh with the actuator third linear gear teeth. It is to be understood that "actuator third linear gear" does not necessarily have to imply that the actuator has three linear gears, especially if the delivery device comprises only one roller. In this case, the "actuator third linear gear" could be one of two actuator linear gears, the other one being the actuator first linear gear. The same applies to the term "seventh gearwheel teeth", which could be one four gearwheels of the first roller.

According to one embodiment the actuator comprises an actuator fourth linear gear provided with actuator fourth linear gear teeth, and wherein the second roller has an eighth gearwheel provided with eighth gearwheel teeth configured to mesh with the actuator fourth linear gear teeth.

According to one embodiment the first compound gear forms part of a first cog axle, and wherein the first roller comprises a first hollow rolling member arranged around the first cog axle, the first hollow rolling member being configured to rotate freely relative to the first cog axle.

According to one embodiment the second compound gear forms part of a second cog axle, and wherein the second roller comprises a second hollow rolling member arranged around the second cog axle, the second hollow rolling member being configured to rotate freely relative to the second cog axle.

According to one embodiment the actuator is a manual button.

One embodiment comprises a motor, wherein the motor is configured to drive the actuator.

One embodiment comprises a resilient member configured to drive the actuator. The resilient member may for example be a spring.

According to one embodiment the delivery device is a medicament delivery device.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the present concept will now be described, by way of example, with reference to the accompanying drawings, in which:

FIG. 2 is an exploded view of the delivery device in FIGS. 1A and 1B;

FIGS. 3A-3B show perspective views of a roller;

DETAILED DESCRIPTION

The present concept will now be described more fully hereinafter with reference to the accompanying drawings, in which exemplifying embodiments are shown. The present concept may, however, be embodied in many different forms and should not be construed as limited to the embodiments set forth herein; rather, these embodiments are provided by way of example so that this disclosure will be thorough and complete, and will fully convey the scope of the present concept to those skilled in the art. Like numbers refer to like members throughout the description.

Figure 1A:
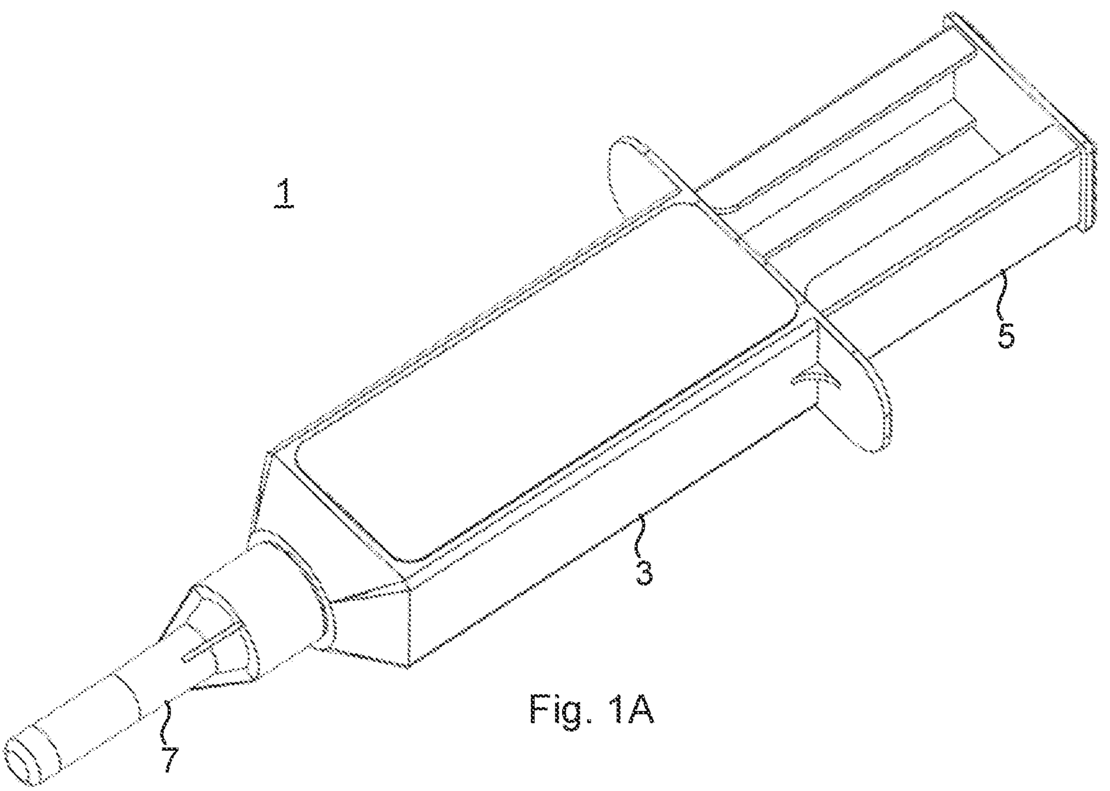
FIG. 1A shows a perspective view of an example of a delivery device with its cap attached before liquid delivery.

FIG. 1 shows an example of a delivery device 1 for delivering liquid from a flexible container. The delivery device 1 will in the following be exemplified by a medicament delivery device. The delivery device could however be configured for delivering any kind of liquid contained in a flexible container. The delivery device could for example be configured to deliver eye drops.

Figure 5A:
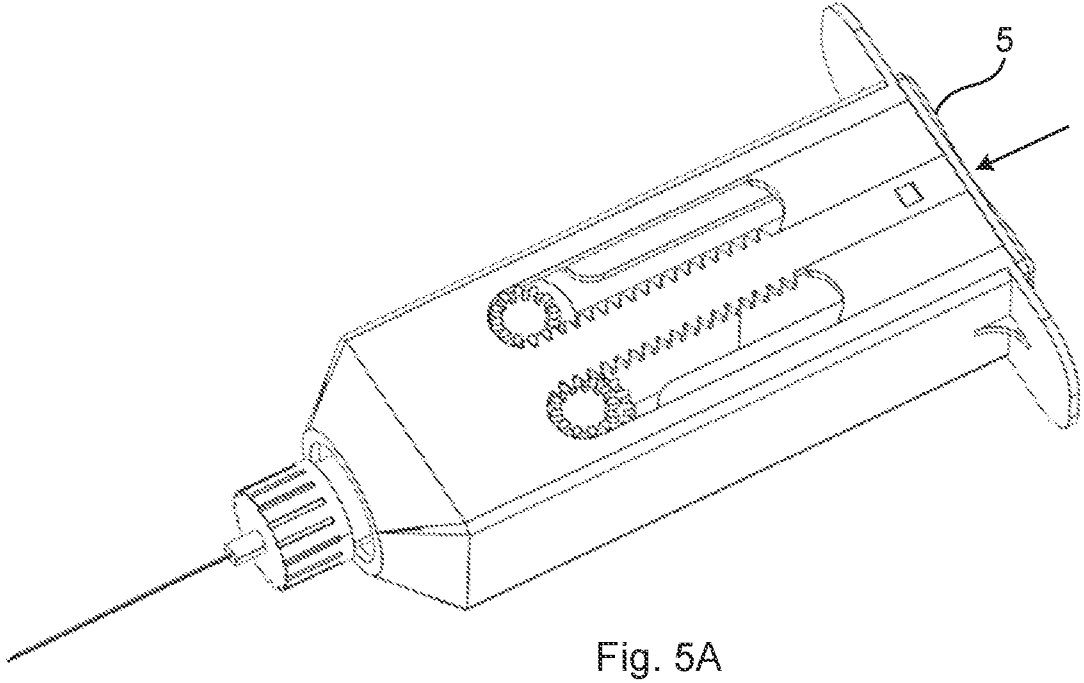
FIG. 5A is a perspective view of the delivery device after liquid delivery has been performed.

The delivery device 1 comprises a housing 3 and an actuator 5. The actuator 5 is configured to be moved linearly inside the housing 3. The actuator 5 is configured to be moved from a first position relative to the housing, as 3 shown in FIG. 1*a*, to a second position as shown in FIG. 5*a*. The first position is an extended position relative to the housing 3 and the second position is a retracted position.

The actuator 5 is in the present example a manual button. The manual button extends from the rear end of the housing 3. The manual button can be pushed into the housing 3 from the first position towards the second position to deliver a liquid contained in a flexible container arranged inside the housing 3.

Figure 1B:
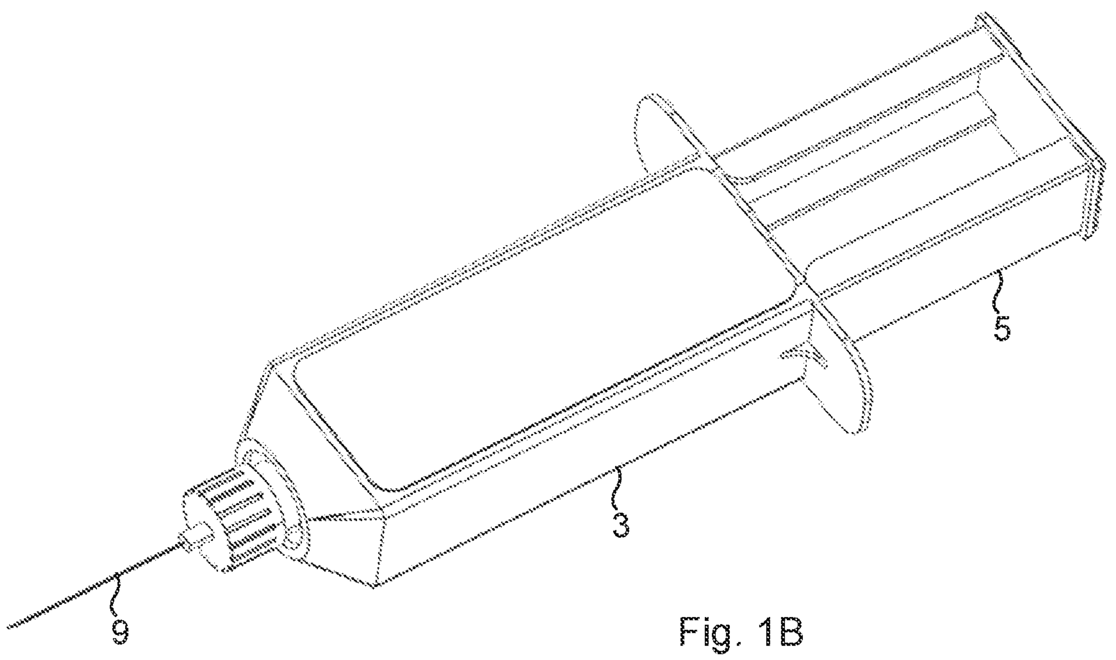
FIG. 1B is a perspective view of the delivery device in FIG. 1A with the cap removed.

The delivery device 1 may comprise a cap 7. The cap 7 is configured to be removably attached to a front end of the housing 3 or to a front end of the flexible container arranged in the delivery device 1. The cap 7 protects a delivery member, such as a needle, of the flexible container. FIG. 1*b* shows the delivery device 1 when the cap 7 has been removed and the needle 9, which extends through the front of the housing 3, has been exposed.

FIG. 2 depicts an exploded view of the delivery device 1. The exemplified delivery device comprises a first roller 11 and a second roller 13. The rollers 11 and 13 are configured to be translated from a rear portion of the housing 3 to a front portion of the housing 3 when the actuator 5 is moved from the first position to the second position. The rollers 11 and 13 are configured to be translated from the front portion back to the rear portion when the actuator 5 is moved back to the first position from the second position.

The first roller 11 comprises a first cog axle 11*a* which on one axial end has a compound gear 11*b* comprising two gearwheels. The exemplified first roller 11 has a single gearwheel 11*c* arranged at the other axial end of the first cog axle 11*a*. The first roller 11 could alternatively have two compound gears, one provided at each axial end thereof.

The first roller 11 comprises a first hollow rolling member 11*d* arranged around the first cog axle 11*a*. The first hollow rolling member 11*d* and the first cog axle 11*a* are arranged concentrically. The first hollow rolling member 11*d* is configured to rotate freely relative to the first cog axle 11*a*.

The second roller 13 comprises a second cog axle 13*a* which on one axial end has a second compound gear 13*b* comprising two gearwheels. This end is arranged in an opposite direction compared to the orientation of the first compound gear 11*b*. The exemplified second roller 13 has a single gearwheel 13*c* arranged at the other end of the second cog axle 13*a*. The axial ends of the first roller 11 and the second roller 13 provided with a single gearwheel side are thus arranged in opposite directions. The second roller 13 could alternatively have two compound gears, one provided at each axial end thereof.

The second roller 13 comprises a second hollow rolling member 13*d* arranged around the second cog axle 13*a*. The second hollow rolling member 13*d* and the second cog axle

13*a* are arranged concentrically. The second hollow rolling member 13*d* is configured to rotate freely relative to the second cog axle 13*a*.

The delivery device 1 comprises a roller stop 15 configured to delimit rearward movement of the first roller 11 and the second roller 13. The roller stop 15 is configured to prevent the first roller 11 and the second roller 13 to move out from the housing 3.

The roller stop 15 may be attached to the housing 3. The roller stop 15 may for example be attached to the housing 3 by means of a snap-fit connection.

The housing 3 comprises a plurality of housing linear gears, or gear racks, 3*a*. The housing linear gears are integrated in the housing 3. The housing linear gears 3*a* extend longitudinally in a direction parallel with the central axis of the delivery device 1, from a front end towards a rear end thereof. Each housing linear gear 3*a* comprises a plurality of housing linear gear teeth.

According to the example shown in FIG. 2, the housing 3 is provided with four housing linear gears 3*a*. The housing 3 has a first wall 3*b* comprising two housing linear gears 3*a*, namely a housing first linear gear 4 provided with housing first linear gear teeth 4*a* and a housing third linear gear 6 provided with housing third linear gear teeth 6*a*. The housing first linear gear 4 and the housing third linear gear 6 extend parallel with each other.

The housing 3 has a second wall 3*c* opposite to the first wall 3*b* comprising two housing linear gears 3*a*, namely a housing second linear gear (not shown) provided with housing second linear gear teeth (not shown) and a housing fourth linear gear 8 provided with housing fourth linear gear teeth 8*a*. The housing second linear gear and the housing fourth linear gear 8 extend parallel with each other. The housing second linear gear is arranged oppositely to and aligned with the housing first linear gear 4. The housing fourth linear gear 8 is arranged oppositely to and aligned with the housing third linear gear 6.

The housing first linear gear teeth 4*a* are configured to mesh with the gearwheel teeth of the outer gearwheel of the first compound gear 11*a*. The housing second linear gear teeth are configured to mesh with the gearwheel teeth of the single gearwheel 11*c* of the first roller 11.

The housing third linear gear teeth 6*a* are configured to mesh with the gearwheel teeth of the outer gearwheel of the second compound gear 13*a*. The housing fourth linear gear teeth 8*a* are configured to mesh with the gearwheel teeth of the single gearwheel 13*c* of the second roller 13. The actuator 5 has a rear end 5*a*, and a first leg 5*b* and a second leg 5*c* extending in the forward direction from the rear end 5*a* in the housing 3.

The first leg 5*b* is provided with an actuator first linear gear, or gear rack, 10, comprising a plurality of actuator first linear teeth 10*a* configured to mesh with the gearwheel teeth of the inner gearwheel of the first compound gear 11*a*.

The second leg 5*c* is provided with an actuator second linear gear, or gear rack, 12, comprising a plurality of actuator second linear teeth 12*a* configured to mesh with the gearwheel teeth the inner gearwheel of the second compound gear 13*a*.

The delivery device 1 may also comprise a flexible container 14. The flexible container 14 may for example be made of a polymer material such as polyethylene or polypropylene. The flexible container 14 may for example be a blow-fill-seal container.

The flexible container 14 may have a flat rear end portion 14*a*. The first roller 11 and the second roller 13 may be arranged at opposite sides of the rear end portion 14*a* when the actuator 5 is in the first position.

The flexible container 14 may comprise a mechanically flexible body 14*b* arranged in the forward direction relative to the rear end portion 14*a*. The mechanically flexible body contains a liquid prior to delivery. The liquid is in the present example a medicament but could alternatively for example be eye drops e.g. water.

As the actuator 5 is moved in the forward direction from the first position towards the second position, the first roller 11 and the second roller 13 move along and in contact with the mechanically flexible body 14*b* from opposing sides, whereby the liquid content is squeezed out through from the flexible container 14 by the translational and rotational movement of the rollers 11 and 13. In the present example, the liquid is squeezed out through the needle 9.

The delivery device 1 may contain side plates 17*a* and 17*b* configured to be arranged on the housing 3 to cover the housing linear gears 3*a*.

FIG. 3*a* shows the first cog axle 11*a*. Both the first cog axle 11*a* and the second cog axle 13*a* may be similar or identical. Therefore, only the first cog axle 11*a* is described. The cog axles 11*a*, 13*a* may be formed as an integral component, for example by moulding.

The first compound gear 11*b* has a first gearwheel 16 provided with first gearwheel teeth 18 and a second gearwheel 20 provided with second gearwheel teeth 22. The first gearwheel 16 is arranged axially outside the second gearwheel 20 and is thus the outer gearwheel of the first compound gear 11*b*. The first gearwheel 16 and the second gearwheel 20 are arranged coaxially and adjacent to each other.

The first gearwheel 16 has a diameter which differs from the diameter of the second gearwheel 20. In this example, the first gearwheel 16 has a smaller diameter than the second gearwheel 20. This results in torque amplification. Alternatively, the first gearwheel could have a larger diameter than the second gearwheel. This results in speed amplification of the movement of the rollers 11, 13 compared to the speed of movement of the actuator 5.

The single gearwheel 11*c* of the first roller 11 is herein also referred to as a third gearwheel. The single gearwheel 13*c* of the second roller 13 is herein also referred to as a fourth gearwheel. The two gearwheels making up the second compound gear 13*b* are herein also referred to as a fifth gearwheel, or outer gearwheel, having fifth gearwheel teeth, and a sixth gearwheel, or inner gearwheel, having sixth gearwheel teeth. In this example, the fifth gearwheel has a smaller diameter than the sixth gearwheel. Alternatively, the fifth gearwheel could have a larger diameter than the sixth gearwheel.

In one variation, the cog axles of both rollers could be provided with compound gears on both axial ends. In this case, that axial end of the first roller provided with the third gearwheel would also have a seventh gearwheel provided with seventh gearwheel teeth and the that axial end of the second roller provide with the fourth gearwheel would also have an eighth gearwheel provided with eighth gearwheel teeth. According to yet another variation, there is only one roller, which on both its axial ends has compound gears with two gearwheels each, i.e. the first gearwheel, the second gearwheel, the third gearwheel and the seventh gearwheel.

In FIG. 3*b* the first hollow rolling member 11*d* is arranged around the first cog axle 11*a*.

Figure 4A:
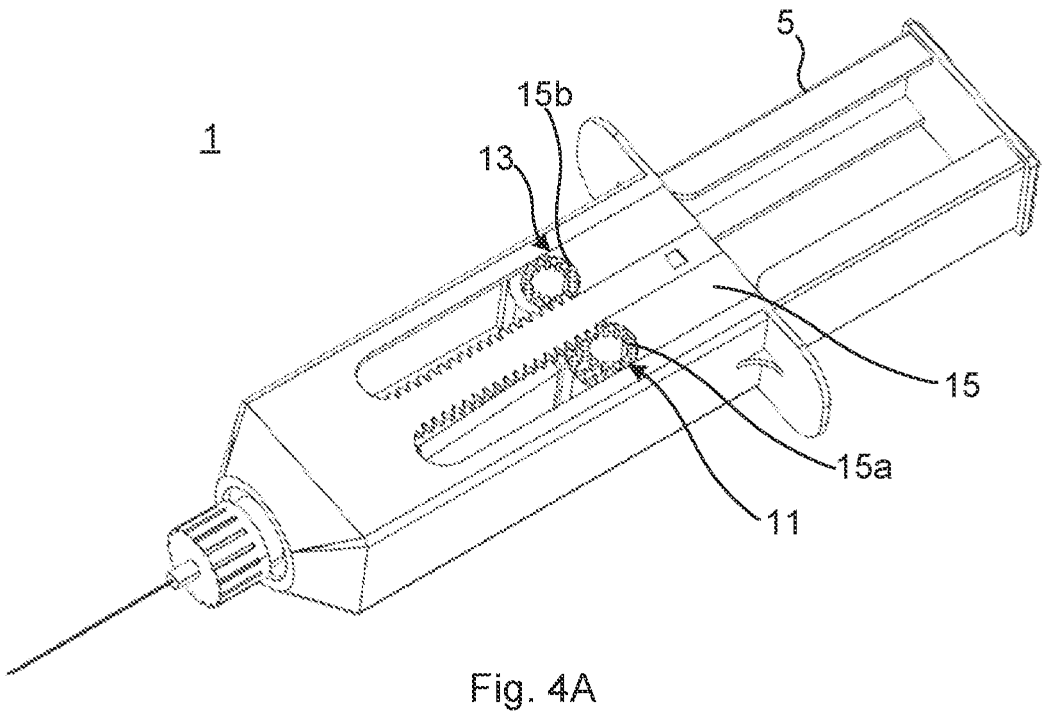
FIG. 4A is a perspective view of the delivery device in FIG. 1 with a side cover removed to expose the interior of the delivery device.

FIG. 4*a* shows a perspective view of the delivery device 1 with the side plates 17*a*, 17*b* removed to expose the interior of the delivery device 1. The delivery device 1 is shown before liquid delivery, when the actuator 5 is in the first position. The gearwheels engage with the respective housing linear gears or with the actuator linear gears. The first roller 11 and the second roller 13 are partly received by a respective recess 15*a* and 15*b* of the roller stop 15. The first roller 11 and the second roller 13 are arranged on either side of the flat rear end portion 14*a* of the flexible container 14.

Figure 4B:
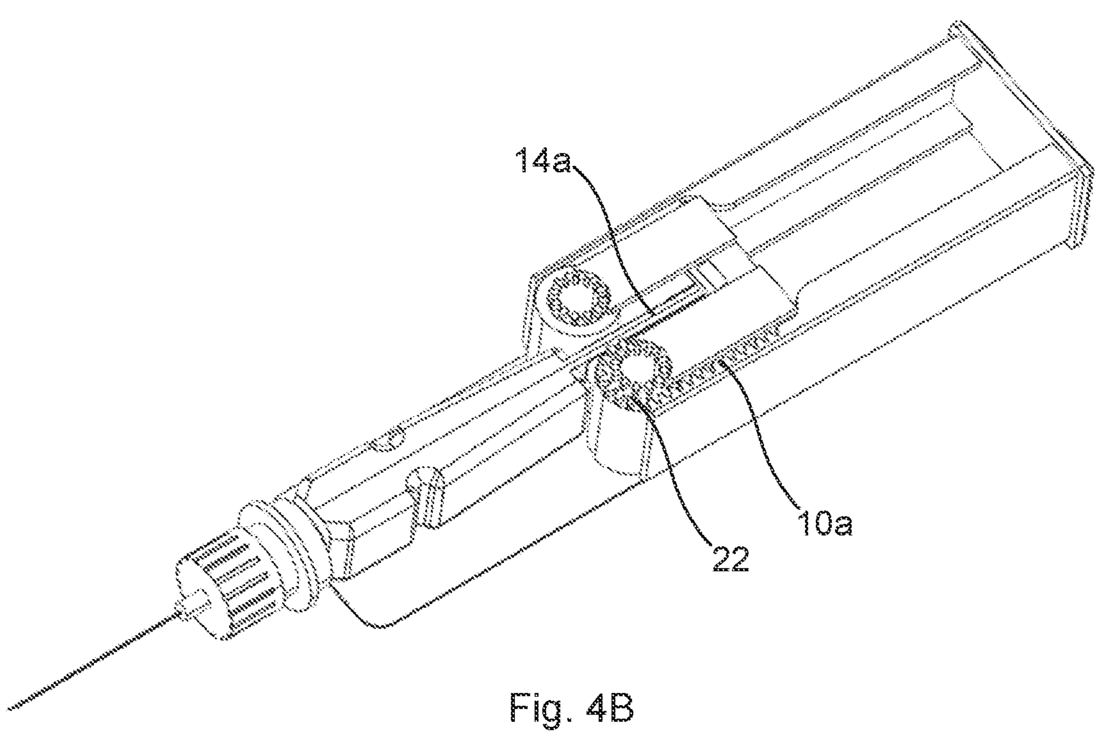
FIG. 4B shows the same view as FIG. 4A but with the housing removed.

As shown in FIG. 4*b*, the second gearwheel teeth 22 engage with the actuator first linear teeth 10.

FIG. 5*a* illustrates when the actuator 5 has been moved from the first position to the second position, i.e. from the extended position to the retracted position. The actuator first linear gear 10 and the actuator second linear gear 12 follow the motion of the actuator 5 and thus cause rotation of the first roller 11 and the second roller 13 when the actuator 5 is being moved. Because, as described above, the gearwheel teeth of some of the gearwheels of the first roller 11 and the second roller 13 mesh with respective housing linear gears 3*a*, the first roller 11 and the second roller 13 move along the housing linear gears 3*a* and thus the flexible container 14 at either side thereof. As the two rollers 11 and 13 move along and in contact with the mechanically flexible body 14*b*, the liquid contained therein is delivered through the needle 9.

Figure 5B:
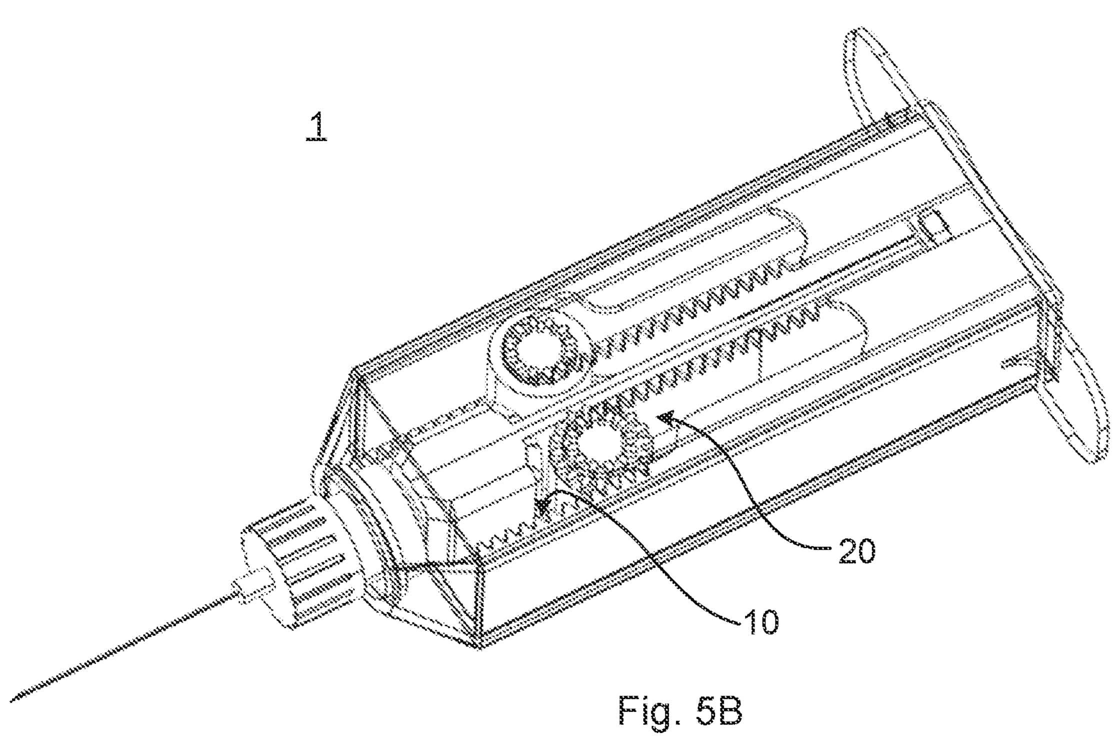
FIG. 5B is the same view as in FIG. 5A but with the housing transparent to show the interior of the delivery device.

FIG. 5*b* shows the delivery device 1 in the same state as in FIG. 5*a* but with the housing 3 transparent to illustrate the interaction between the actuator first linear gear 10 and the second gearwheel 20.

The actuator 5 described above is manual and in the form of a manual button which can be actuated by a user by pushing the button into the housing 3 to cause movement from the first position to the second position or by pulling the button out from the housing 3 to cause movement from the second position to the first position.

According to one example, the delivery device may comprise a motor, wherein the actuator may be configured to be driven by the motor to move between the first position and the second position.

According to one example, the delivery device may comprise one or more resilient members such as one or more coil springs storing energy in the first position of the actuator. When the energy is released, the resilient member drives the actuator from the first position to the second position.

The present concept has mainly been described above with reference to a few examples. However, as is readily appreciated by a person skilled in the art, other embodiments than the ones disclosed above are equally possible within the scope of the present concept, as defined by the appended claims.

The invention claimed is:

1. A delivery device for delivering liquid from a flexible container, the delivery device comprising:

a housing having a first wall provided with a housing first linear gear having housing first linear gear teeth, the housing being configured to receive the flexible container, a first roller having a first compound gear comprising a first gearwheel provided with first gearwheel teeth and a second gearwheel provided with second gearwheel teeth, and an actuator comprising an actuator first linear gear provided with actuator first linear gear teeth, wherein the first gearwheel teeth are configured to mesh with the housing first linear gear teeth and the second gearwheel teeth are configured to mesh with the actuator first linear gear teeth, wherein the actuator is configured to be moved linearly from a first position to a second position along a longitudinal axis defined by a longitudinal extension of the housing first linear gear, causing the first roller to be translated along the housing first linear gear, to squeeze liquid from the flexible container, wherein a diameter of the first gearwheel is smaller than that of the second gearwheel.

2. The delivery device as claimed in claim 1, wherein the housing has a second wall, opposite to the first wall, provided with a housing second linear gear having housing second linear gear teeth, and wherein the first roller has a third gearwheel provided with third gearwheel teeth configured to mesh with the housing second linear gear teeth.

3. The delivery device as claimed in claim 2, wherein the first wall is provided with a housing third linear gear arranged parallel with the housing first linear gear, the housing third linear gear being provided with housing third linear gear teeth, wherein the delivery device comprises a second roller arranged parallel with the first roller and having a fourth gearwheel provided with fourth gearwheel teeth configured to mesh with the housing third linear gear teeth.

4. The delivery device as claimed in claim 3, wherein the second wall is provided with a housing fourth linear gear arranged parallel with the housing second linear gear, the housing fourth linear gear being provided with housing fourth linear gear teeth, wherein the second roller has a second compound gearwheel comprising a fifth gearwheel provided with fifth gearwheel teeth and a sixth gearwheel provided with sixth gearwheel teeth, wherein the actuator has an actuator second linear gear provided with actuator second linear gear teeth, wherein the fifth gearwheel teeth are configured to mesh with the housing fourth linear gear teeth and the sixth gearwheel teeth are configured to mesh with the actuator second linear gear teeth, wherein movement of the actuator from the first position to the second position causes the second roller to be translated along the housing second linear gear to squeeze liquid from the flexible container from an opposite side relative to the first roller, and wherein a diameter of the fifth gearwheel differs from that of the sixth gearwheel.

5. The delivery device as claimed in claim 4, wherein the diameter of the fifth gearwheel is smaller than that of the sixth gearwheel.

6. The delivery device as claimed in claim 1, wherein the first compound gear forms part of a first cog axle, and wherein the first roller comprises a first hollow rolling member arranged around the first cog axle, the first hollow rolling member being configured to rotate freely relative to the first cog axle.

7. The delivery device as claimed in claim 4, wherein the second compound gear forms part of a second cog axle, and wherein the second roller comprises a second hollow rolling member arranged around the second cog axle, the second hollow rolling member being configured to rotate freely relative to the second cog axle.

8. The delivery device as claimed in claim 1, wherein the actuator is a manual button.

9. The delivery device as claimed in claim 1, comprising a motor, wherein the motor is configured to drive the actuator.

10. The delivery device as claimed in claim 1, comprising a resilient member configured to drive the actuator.

11. The delivery device as claimed in claim 1, wherein the delivery device is a medicament delivery device.

12. A delivery device for delivering liquid comprising:

a flexible container containing the liquid;

a housing having a first wall provided with a housing first linear gear having housing first linear gear teeth and a second wall provided with a housing second linear gear having housing second linear gear teeth, where the housing is configured to receive the flexible container;

a first roller having a first compound gear comprising a first gearwheel provided with first gearwheel teeth, a second gearwheel provided with second gearwheel teeth and a third gearwheel in rotating engagement with the housing second linear gear teeth; and an actuator comprising an actuator first linear gear provided with actuator first linear gear teeth, wherein the first gearwheel teeth are configured to mesh with the housing first linear gear teeth and the second gearwheel teeth are configured to mesh with the actuator first linear gear teeth, wherein the actuator is configured to be moved linearly from a first position to a second position along a longitudinal axis defined by a longitudinal extension of the housing first linear gear, causing the first roller to be translated along the housing first linear gear, to squeeze liquid from the flexible container, wherein the first gearwheel has a diameter which is less than that of the second gearwheel.

13. The delivery device of claim 12, wherein the first wall further comprises a housing third linear gear having a housing third linear gear teeth arranged parallel with the housing first linear gear.

14. The delivery device of claim 13, wherein the delivery device further comprises a second roller arranged parallel with the first roller and having a fourth gearwheel provided with fourth gearwheel teeth that mesh with the housing third linear gear teeth.

15. The delivery device of claim 14, wherein the actuator further comprises an actuator second linear gear provided with actuator second linear gear teeth that extends in the same direction as the actuator first linear gear.

16. The delivery device of claim 15, wherein the second roller comprises three gears with one of the three gears being in meshed engagement with the actuator second linear gear.

17. The delivery device of claim 14, wherein the first roller and the second roller are each hollow and supported by a first cog axle and a second cog axle, respectively.

* * * * *